US012329905B2

(12) United States Patent
Oates et al.

(10) Patent No.: US 12,329,905 B2
(45) Date of Patent: *Jun. 17, 2025

(54) FLOW GENERATOR MESSAGE SYSTEM

(71) Applicant: ResMed Pty Ltd, Bella Vista (AU)

(72) Inventors: John David Oates, Sydney (AU);
Mark David Buckley, Sydney (AU);
Philip Rodney Kwok, Sydney (AU);
Mark Alexander Abourizk, Sydney (AU); Thomas Evan Miller, Pittsford, NY (US); Simone Marie Jeha, Sydney (AU); Mark John Payne, Gosford (AU); Muditha Pradeep Dantanarayana, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 1073 days.

This patent is subject to a terminal disclaimer.

(21) Appl. No.: 17/302,707

(22) Filed: May 11, 2021

(65) Prior Publication Data

US 2021/0260315 A1 Aug. 26, 2021

Related U.S. Application Data

(60) Continuation of application No. 16/103,258, filed on Aug. 14, 2018, now Pat. No. 11,033,699, which is a (Continued)

(51) Int. Cl.
*A61M 16/00* (2006.01)
*A61M 16/06* (2006.01)
(Continued)

(52) U.S. Cl.
CPC .... *A61M 16/0057* (2013.01); *A61M 16/0003* (2014.02); *A61M 16/0051* (2013.01); (Continued)

(58) Field of Classification Search
CPC .............. A61M 16/00; A61M 16/0003; A61M 16/0051; A61M 16/0057; A61M 16/0066;
(Continued)

(56) References Cited

U.S. PATENT DOCUMENTS

| 2,598,978 A | 6/1952 | Martin |
| 4,883,051 A | 11/1989 | Westenskow |

(Continued)

FOREIGN PATENT DOCUMENTS

| AU | 2016/101312 | 8/2016 |
| EP | 1127583 | 7/2003 |

(Continued)

OTHER PUBLICATIONS

Amended Notice of Opposition to Grant of Patent and Statement of Case issued Feb. 29, 2012 for corresponding New Zealand Application No. 567371.

(Continued)

*Primary Examiner* — Annette Dixon
(74) *Attorney, Agent, or Firm* — Nixon & Vanderhye PC

(57) ABSTRACT

A flow generator for delivering breathable gas to a patient includes a processor coupled with operation sensors and a user interface. The processor is programmed to generate at least one of time-based or event-based messages relating to at least one of flow generator operation, flow generator service, flow generator use, patient health, peripheral devices and services, patient treatment, and reminders. Time-based messages are generated at predetermined time intervals based on either time of use or elapsed time. The event-based messages are generated based on signals from the operation sensors. The user interface is configured to deliver the messages to at least one of a display, a flow (Continued)

generator service provider, the patient and a physician. By this system, operation of the flow generator is facilitated and enhanced.

20 Claims, 2 Drawing Sheets

Related U.S. Application Data continuation of application No. 14/665,192, filed on Mar. 23, 2015, now Pat. No. 10,076,617, which is a continuation of application No. 13/845,413, filed on Mar. 18, 2013, now Pat. No. 9,010,328, which is a division of application No. 12/067,234, filed as application No. PCT/AU2006/001506 on Oct. 13, 2006, now Pat. No. 8,424,514.

(60) Provisional application No. 60/726,178, filed on Oct. 14, 2005.

(51) Int. Cl.
    *A61M 16/08*     (2006.01)
    *H04L 67/125*     (2022.01)

(52) U.S. Cl.
    CPC ...... *A61M 16/0066* (2013.01); *A61M 16/024* (2017.08); *A61M 16/0616* (2014.02); *A61M 16/0875* (2013.01); *H04L 67/125* (2013.01); *A61M 2205/18* (2013.01); *A61M 2205/3334* (2013.01); *A61M 2205/3546* (2013.01); *A61M 2205/3561* (2013.01); *A61M 2205/3584* (2013.01); *A61M 2205/502* (2013.01); *A61M 2205/52* (2013.01)

(58) Field of Classification Search
    CPC ............ A61M 16/0069; A61M 16/024; A61M 16/026; A61M 16/0616; A61M 16/0666; A61M 16/0816; A61M 16/0833; A61M 16/0858; A61M 16/0875; A61M 16/107; A61M 16/125; A61M 16/16; A61M 16/202; A61M 16/204; A61M 16/205; A61M 2016/0021; A61M 2016/0027; A61M 2016/0033; A61M 2016/0036; A61M 2016/0039; A61M 2016/0042; A61M 2205/15; A61M 2205/18; A61M 2205/3334; A61M 2205/3365; A61M 2205/3546; A61M 2205/3561; A61M 2205/3584; A61M 2205/50; A61M 2205/502; A61M 2205/505; A61M 2205/52; A61M 2205/60; A61M 2205/6018; A61M 2205/6027; A61M 2205/6045; A61M 2230/10; A61M 2230/18; A61M 2230/60; A61M 2230/63; F04D 25/166; F04D 29/052; F04D 29/286; H04L 67/125
See application file for complete search history.

(56) References Cited

U.S. PATENT DOCUMENTS

| | | | |
|---|---|---|---|
| 5,072,728 A | 12/1991 | Pasternack | |
| 5,413,097 A | 5/1995 | Birenheide | |
| 5,490,502 A | 2/1996 | Rapoport et al. | |
| 5,503,146 A | 4/1996 | Froehlich et al. | |
| 5,844,862 A | 12/1998 | Cocatre-Zilgien | |
| 5,895,595 A | 4/1999 | Haden | |
| 5,950,621 A | 9/1999 | Klockseth | |
| 6,085,747 A | 7/2000 | Axe et al. | |
| 6,119,686 A | 9/2000 | Somerson et al. | |
| 6,302,105 B1 | 10/2001 | Wickham | |
| 6,349,724 B1 * | 2/2002 | Burton | A61M 16/0057 128/204.22 |
| 6,360,741 B2 | 3/2002 | Truschel | |
| 6,363,933 B1 | 4/2002 | Berthon-Jones | |
| 6,425,395 B1 | 7/2002 | Brewer et al. | |
| 6,543,449 B1 | 4/2003 | Woodring | |
| 6,546,930 B1 | 4/2003 | Emerson et al. | |
| 6,678,215 B1 | 1/2004 | Treyz et al. | |
| 6,723,055 B2 | 4/2004 | Hoffman | |
| 6,953,354 B2 | 10/2005 | Edirisuriya et al. | |
| 7,148,806 B2 | 12/2006 | Anttila | |
| 7,314,451 B2 | 1/2008 | Halperin et al. | |
| 7,617,824 B2 | 11/2009 | Doyle | |
| 8,186,345 B2 | 5/2012 | Payton et al. | |
| 8,424,514 B2 * | 4/2013 | Oates | A61M 16/0616 128/200.24 |
| 9,162,035 B2 | 10/2015 | Kwok | |
| 10,533,940 B2 | 1/2020 | Manassen et al. | |
| 2001/0017134 A1 | 8/2001 | Bahr | |
| 2002/0022973 A1 | 2/2002 | Sun et al. | |
| 2002/0088464 A1 | 7/2002 | Truschel | |
| 2003/0076745 A1 | 4/2003 | Chapman | |
| 2003/0140924 A1 | 7/2003 | Aylsworth et al. | |
| 2003/0187525 A1 | 10/2003 | Mann et al. | |
| 2003/0208465 A1 | 11/2003 | Yurko et al. | |
| 2003/0236450 A1 | 12/2003 | Kocinski | |
| 2004/0118403 A1 | 6/2004 | O'Conner et al. | |
| 2005/0076906 A1 | 4/2005 | Johnson | |
| 2005/0114182 A1 | 5/2005 | Randolph et al. | |
| 2005/0217672 A1 | 10/2005 | Bengtsson | |
| 2008/0078387 A1 | 4/2008 | Vandine | |
| 2009/0120437 A1 | 5/2009 | Oates | |
| 2011/0232645 A1 | 9/2011 | Smith | |
| 2013/0206143 A1 | 8/2013 | Oates et al. | |
| 2015/0196725 A1 | 7/2015 | Oates | |

FOREIGN PATENT DOCUMENTS

| | | |
|---|---|---|
| EP | 1 449 558 | 8/2004 |
| JP | H6-23051 | 2/1994 |
| WO | 1990/014121 | 11/1990 |
| WO | 96/28093 | 9/1996 |
| WO | 1997/006843 | 2/1997 |
| WO | 1998/041279 | 9/1998 |
| WO | 1999/043388 | 9/1999 |
| WO | 2000/069337 | 11/2000 |
| WO | 2001/000264 | 1/2001 |
| WO | 2001/32069 | 5/2001 |
| WO | 2001/91841 | 12/2001 |
| WO | 2002/02169 | 1/2002 |
| WO | 2002/047747 | 6/2002 |
| WO | 2004/049912 | 6/2004 |
| WO | 2005/011556 | 2/2005 |
| WO | 2005/037355 | 4/2005 |
| WO | 2013/151488 | 10/2013 |
| WO | 2015/060729 | 4/2015 |

OTHER PUBLICATIONS

International Search Report for PCT/AU2006/001506 mailed Jan. 30, 2007.
Written Opinion of the International Searching Authority for PCT/AU2006/001506, mailed Jan. 30, 2007.
International Preliminary Report on Patentability for PCT/AU2006/001506, mailed Jan. 30, 2007.
Amended Notice of Opposition to Grant a Patent, filed on Jan. 28, 2014 in New Zealand Application No. 591993.
U.S. Appl. No. 60/656,880, filed Mar. 2005, Kwok.
U.S. Appl. No. 60/703,432, filed Jul. 2005, Kwok et al.
Statement Of Case, filed on Jan. 28, 2014 in New Zealand Application No. 591993.
"Alarm Clock". The Penguin English Dictionary. 2007. http://www.credoreference.com/entry/penguineng/alarm_clock (Sep. 30, 2013).
Second Amended Notice of Opposition to Grant a Patent, filed on Jul. 18, 2014 in New Zealand Application No. 591993.

(56) References Cited

OTHER PUBLICATIONS

Amended Statement Of Case, filed on Jul. 18, 2014 in New Zealand Application No. 591993.
Statutory Declaration of Ian Malcolm Smith filed on May 28, 2015 in New Zealand Application No. 591993.
Statutory Declaration of Professor Geoffrey Mark Shaw filed on May 28, 2015 in New Zealand Application No. 591993.
Statutory Declaration of Haydn Llewellyn filed on Sep. 25, 2015 in New Zealand Application No. 591993.
Affirmation of Yi-Cheng Sun filed on Feb. 9, 2016 in New Zealand Application No. 591993.
Affirmation of Dr. David Maurice Rapoport filed on Feb. 9, 2016 in New Zealand Application No. 591993.
First Amended Notice of Opposition to Grant of Patent, filed on Mar. 29, 2016 in New Zealand Application No. 700746.
Statement of Case, filed on Mar. 29, 2016 in New Zealand Application No. 700746.
Amended Statement of Case No. NZ 700746 dated Mar. 2, 2017 (6 pages).
Affirmation of Ian Douglas Makinson dated Jan. 26, 2017 (14 pages).
Affirmation of Andrew Baden Clark dated Feb. 3, 2017 (14 pages).
Affirmation of Andrew Michael Baker dated Feb. 3, 2017 (26 pages).
Second Amended Statement Of Case, filed on Sep. 29, 2014 in New Zealand Application No. 591993.
Statutory Declaration of Alex Young filed on Sep. 29, 2014 in New Zealand Application No. 591993.
Statutory Declaration of Andrew Baden Clark filed on Sep. 29, 2014 in New Zealand Application No. 591993.
Statutory Declaration of David Robin Whiting filed on Sep. 29, 2014 in New Zealand Application No. 591993.
Amended Counterstatement, filed on Aug. 21, 2014 in New Zealand Application No. 591993.
Statutory Declaration of Andrew Baden Clark, filed on Sep. 8, 2014 in New Zealand Application No. 600480.
Statutory Declaration of Haydn Llewellyn, filed on Sep. 8, 2014 in New Zealand Application No. 600480.
Second Amended Notice of Opposition to Grant a Patent, filed on Sep. 8, 2014 in New Zealand Application No. 600480.
Amended Statement Of Case, filed on Sep. 8, 2014 in New Zealand Application No. 600480.
Amended Counterstatement, filed on Oct. 15, 2014 in New Zealand Application No. 600480.
Third Amended Notice of Opposition to Grant of Patent, filed on Oct. 21, 2014 in New Zealand Application No. 591993.
Third Amended Statement of Case, filed on Oct. 21, 2014 in New Zealand Application No. 591993.
Proceeding Correspondence in NZ Appln. No. 591993 dated Oct. 30, 2017 (1 page).
Applicant's Response to Examiners Report on Latest Proposed Claim Amendments in NZ Appln. No. 591993 dated Oct. 24, 2017 (4 pages).
Amended Claims in Applicant's Response to Examiners Report on Latest Proposed Claim Amendments in NZ Appln. No. 591993 dated Oct. 24, 2017 (3 pages).
Examiners Report on Revised Proposed Claim Amendments in NZ Appln. No. 5919933 dated Sep. 25, 2017 (4 pages).
Proceeding Correspondence in NZ Appln. No. 700746 dated Oct. 3, 2017 (1 page).
Applicant's Response to Examiners Report on Proposed Claim Amendments in NZ Appln. No. 700746 dated Sep. 28, 2017 (1 page).
Amended Claims in Applicant's Response to Examiners Report on Proposed Claim Amendments in NZ Appln. No. 700746 dated Sep. 28, 2017 (3 pages).
Proceeding Correspondence in NZ Appln. No. 700746 dated Sep. 19, 2017 (2 pages).
Response to Examiner's Report in in NZ Appln. No. 591993 dated Aug. 18, 2017 (2 pages).
Amended Claims Response to Examiner's Report in in NZ Appln. No. 591993 dated Aug. 18, 2017 (3 pages).
Proceeding Correspondence in NZ Appln. No. 591993 dated Aug. 28, 2017 ( 1 page).
Proceeding Correspondence in NZ Appln. No. 591993 dated Jul. 20, 2017 (1 page).
Examiners Report on Amendments in Proceeding Correspondence in NZ Appln. No. 591993 dated Jul. 20, 2017 (2 pages).
Claims in Examiners Report on Amendments in Proceeding Correspondence in NZ Appln. No. 591993 dated Jul. 20, 2017 (3 pages).
Proceeding Correspondence in Amended Counterstatement in NZ Appln. No. 700746 dated Jun. 26, 2017 (1 page).
Amended Counterstatement in NZ Appln. No. 700746 dated Jun. 26, 2017 (14 pages).
Amended Claims in Amended Counterstatement in NZ Appln. No. 700746 dated Jun. 26, 2017 (3 pages).
Request for Change of Inventorship Declined in NZ Appln. No. 711441 dated Feb. 16, 2017 (2 pages).
Response to Request for Change of Inventorship Declined in NZ Appln. No. 711441 dated Feb. 27, 2017 (1 page).
Request for Change of Inventorship Declined in NZ Appln. No. 711441 dated Mar. 9, 2017 (1 pages).
Response to Declining of Change of Inventorship dated in NZ Appln. No. 711441 Mar. 14, 2017 (2 pages).
Correspondence re Correction of Error in NZ Appln. No. 711441 dated May 10, 2017 (2 pages).
Correspondence re Request for Correction of Error NZ Appln. No. 711441 dated Mar. 30, 2017 (1 page).
Declaration in Support of Correspondence re Request for Correction of Error NZ Appln. No. 711441 dated May 10, 2017 (2 pages).
Correspondence re Applicant's Proposed Claim Amendments in NZ Appln. No. 591993 dated May 15, 2017 (2 pages).
Applicant's Proposed Claim Amendments NZ Appln. No. 591993 dated May 15, 2017 (3 pages).
First Examination Report in NZ Appln. No. 729116 dated May 22, 2017 (3 pages).
Further Examination Report in NZ Appln. No. 711441 dated May 22, 2017 (2 pages).
USPTO Patent Trial and Appeal Board Case IPR2016-01723 dated Mar. 9, 2017 (18 pages).
Second Amended Counterstatement in NZ Application No. 700746 dated Dec. 12, 2017 (17 pages).
Third Amended Notice of Opposition and Second Amended Statement of Case in NZ Application No. 700746 dated Jan. 23, 2018 (2 pages).
Second Amended Statement of Case dated Jan. 23, 2018 (20 pages).
Proceeding Correspondence in Application No. 591993 dated Jan. 31, 2018 (2 pages).
4th Amended Statement of Case in NZ application No. 591993 dated Apr. 13, 2018 (17 pages).
International Standard, IEC 60601-1-8, First Edition, dated Aug. 2003 (78 pages).
Pulmonetic Systems Innovations for Life, LTV Series Ventilators Operators Manual, dated Apr. 2004 (282 pages).
Proceeding Correspondence in Application No. 591993 dated Apr. 24, 2018 (2 pages).
Proceeding Correspondence in NZ Application No. 700746 dated Aug. 10, 2018 (3 pages).
Proposed Claim Amendments in NZ Application No. 700746 dated Sep. 7, 2018 (4 pages).
Response to Applicant's Proposed Amendments in NZ Application No. 700746 dated Aug. 3, 2018 (2 pages).
First Examination Report in NZ Application No. 747190 dated Oct. 16, 2018 (3 pages).
Proceeding Correspondence in NZ Application No. 591993, dated Aug. 31, 2018, 6 pages (4403-2084).
Proceeding Correspondence and Applicant's Response to Examiner's Report on Latest Proposed Claim Amendments with tracked changes in NZ Application No. 591993, dated Sep. 27, 2018, 6 pages (4403-2084).
Applicant's Response to Examiner's Comments on Latesr Proposed Claim Amendments in NZ Application No. 591993 with tracked changes dated Oct. 15, 2018, 11 pages (4403-2084).

(56) References Cited

OTHER PUBLICATIONS

First Examination Report in AU Application No. 2014337787 dated Jun. 26, 2018, 6 pages (4403-2084).
International Preliminary Report on Patentability and Written Opinion in Application No. PCT/NZ2014/000220 dated Apr. 26, 2016, 9 pages (4403-2084).
Applicant's Response to Examiner's Comments and Proposes Further Claim Amendments in NZ Application No. 591993 with tracked changes dated Jan. 4, 2019, 15 pages (4403-2084).
Proceeding Halt Extended in NZ Application No. 591993 dated May 17, 2019, 1 page (4403-2084).
Further Examination Report in NZ Application No. 700746 dated Jun. 30, 2015, 2 pages (4403-2812).
Response to Examination Report in NZ Application No. 700746 dated Aug. 4, 2015, 24 pages (4403-2812).
Third Affirmation of Alex Young in NZ Application No. 700746 dated Mar. 14, 2018, 4 pages (4403-2812).
Proposed Claim Amendments in NZ Application No. 700746 dated Jul. 4, 2018, 6 pages (4403-2812).
Proceeding Correspondence in NZ Application No. 700746 dated Jul. 5, 2018, 2 pages (4403-2812).
Proceeding Correspondence in NZ Application No. 700746 dated Aug. 10, 2018, 3 pages, (4403-2812).
Examiners Assessment of Proposed Amendments in NZ Application No. 700746 dated Nov. 8, 2018, 3 pages (4403-2812).
Proceeding Halt Extended in NZ Application No. 700746 dated May 17, 2019, 1 page (4403-2812).
Proceeding Correspondence in NZ Application No. 591993, dated Dec. 20, 2019, 7 pages (4403-2084).
Proceeding Correspondence in NZ Application No. 591993, one page, dated Apr. 24, 2020 (N&V Ref.: 4403-2084).
Proceeding Correspondence in NZ Application No. 591993, one page, dated Jul. 22, 2020 (N&V Ref.: 4403-2084).
Proceeding Correspondence in NZ Application No. 591993, two pages, dated Aug. 20, 2020 (N&V Ref.: 4403-2084).
Proceeding Correspondence in NZ Application No. 591993, one page, dated Oct. 1, 2020 (N&V Ref.: 4403-2084).
Follow-Up Applicant Response To Examiner's Comments And Proposed Further Claim Amendments for NZ Application No. 591993, one page, dated Jul. 2, 2020 (N&V Ref.: 4403-2084).
Applicant Responds To Examiner's Comments And Proposes Further Claim Amendments for NZ Application No. 591993, four pages, dated Sep. 18, 2020 (N&V Ref.: 4403-2084).
First Examination Report, for NZ Application No. 762904, three pages, dated Apr. 22, 2020 (N&V Ref.: 4403-3976).
Response to First Examination Report, for NZ Application No. 762904, four pages, dated Jul. 6, 2020 (N&V Ref.: 4403-3976).
Correction of Inventorship for NZ Application No. 762904, one page, dated Jul. 6, 2020 (N&V Ref.: 4403-3976).
Declaration as to Inventorship for NZ Application No. 762904, two pages, filed Jul. 6, 2020 (N&V Ref.: 4403-3976).
Request for Correction of Error—Accepted for NZ Application No. 762904, one page, dated Jul. 7, 2020 (N&V Ref.: 4403-3976).
Further Examination Report, for NZ Application No. 762904, two pages, dated Jul. 17, 2020 (N&V Ref.: 4403-3976).
Response to Further Examination Report, for NZ Application No. 762904, four pages, dated Aug. 28, 2020 (N&V Ref.: 4403-3976).
Further Examination Report, Postponed Acceptance for NZ Application No. 762904, one page, dated Sep. 30, 2020 (N&V Ref.: 4403-3976).
Notice of Acceptance for NZ Application No. 762904, one page, dated Oct. 9, 2020 (N&V Ref.: 4403-3976).
First Examination Report for NZ Application No. 765654, three pages, dated Jul. 16, 2020 (N&V Ref.: 4403-3977).
Response to First Examination Report for NZ Application No. 765654, five pages, dated Sep. 29, 2020 (N&V Ref.: 4403-3977).
Correction of Inventorship for NZ Application No. 765654, two pages, dated Sep. 29, 2020 (N&V Ref.: 4403-3977).
Declaration as to Inventorship for NZ Application No. 765654, two pages, filed Sep. 29, 2020 (N&V Ref.: 4403-3977).
First Examination Report for NZ Application No. 765032, three pages, dated Jul. 16, 2020 (N&V Ref.: 4403-3978).
Response to First Examination Report for NZ Application No. 765032, four pages, dated Oct. 6, 2020 (N&V Ref.: 4403-3978).
Correction of Inventorship for NZ Application No. 765032, two pages, dated Oct. 6, 2020 (N&V Ref.: 4403-3978).
Declaration as to Inventorship for NZ Application No. 765032, two pages, filed Oct. 6, 2020 (N&V Ref.: 4403-3978).
First Examination Report for NZ Application No. 765702, three pages, dated Jul. 16, 2020 (N&V Ref.: 4403-4039).
Response to First Examination Report for NZ Application No. 765702, five pages, dated Oct. 7, 2020 (N&V Ref.: 4403-4039).
Correction of Inventorship for NZ Application No. 765702, two pages, dated Oct. 7, 2020 (N&V Ref.: 4403-4039).
Declaration as to Inventorship for NZ Application No. 765702, two pages, filed Oct. 7, 2020 (N&V Ref.: 4403-4039).
First Examination Report for NZ Application No. 765509, three pages, dated Jul. 16, 2020 (N&V Ref.: 4403-4040).
Response to First Examination Report for NZ Application No. 765509, four pages, dated Oct. 7, 2020 (N&V Ref.: 4403-4040).
Correction of Inventorship for NZ Application No. 765509, two pages, dated Oct. 7, 2020 (N&V Ref.: 4403-4040).
Declaration as to Inventorship for NZ Application No. 765509, two pages, filed Oct. 7, 2020 (N&V Ref.: 4403-4040).
First Examination Report for NZ Application No. 767500, three pages, dated Sep. 18, 2020 (N&V Ref.: 4403-4121).
Response to First Examination Report for NZ Application No. 767500, three pages, dated Oct. 23, 2020 (N&V Ref.: 4403-4121).
Correction of Inventorship for NZ Application No. 767500, two pages, dated Oct. 23, 2020 (N&V Ref.: 4403-4121).
Declaration as to Inventorship for NZ Application No. 767500, two pages, dated Oct. 23, 2020 (N&V Ref.: 4403-4121).
Further Examination Report for NZ Application No. 765032, two pages, dated Nov. 4, 2020 (N&V Ref.: 4403-3978).
Further Examination Report for NZ Application No. 765509, two pages, dated Nov. 5, 2020 (N&V Ref.: 4403-4040).
Request for Correction of Error—Accepted for NZ Application No. 765509, one page, dated Nov. 19, 2020 (N&V Ref.: 4403-4040).
Proceeding Correspondence for NZ Application No. 591993, two pages, dated Nov. 24, 2020 (N&V Ref.: 4403-2084).
Request to Withdraw Patent Application—Accepted for NZ Application No. 591993, one page, dated Nov. 25, 2020 (N&V Ref.: 4403-2084).
Notice of Acceptance for NZ Application No. 767500, one page, dated Nov. 25, 2020 (N&V Ref.: 4403-4121).
Further Examination Report—Postponed Acceptance for NZ Application No. 765702, one page, dated Nov. 6, 2020 (N&V Ref.: 4403-4039).
Request for Correction of Error—Accepted for NZ Application No. 765702, one page, dated Nov. 19, 2020 (N&V Ref.: 4403-4039).
Response to Examination Report for NZ Application No. 765654, two pages, dated Nov. 20, 2020 (N&V Ref.: 4403-3977).
FPH Letter Withdrawing Request of Postponement of Acceptance for FPH Australian Appln. No. 2019204410 (N&V NZ Application No. 591993), one page, dated Nov. 6, 2020 (N&V Ref.: 4403-2084).
Proceeding Correspondence for NZ Application No. 591993, one page, dated Nov. 16, 2020 (N&V Ref.: 4403-2084).
Denton's Response to Applicant's Proposed Amendments for NZ Application No. 591993, three pages, dated Nov. 6, 2020 (N&V Ref.: 4403-2084).
Further Examination Report—Postponed Acceptance for NZ Application No. 767500, one page, dated Nov. 12, 2020 (N&V Ref.: 4403-4121).
Request for Correction of Error—Accepted for NZ Application No. 767500, one page, dated Nov. 11, 2020 (N&V Ref.: 4403-4121).
Further Examination Report for NZ Application No. 765654, two pages, dated Oct. 8, 2020 (N&V Ref.: 4403-3977).
Proceeding Correspondence for NZ Application No. 591993, one page, dated Oct. 30, 2020 (N&V Ref.: 4403-2084).
Denton's Response to Applicant's Proposed Amendments for NZ Application No. 591993, one page, dated Oct. 14, 2020 (N&V Ref.: 4403-2084).

(56) References Cited

OTHER PUBLICATIONS

Further Examination Report for NZ Application No. 765654, two pages, dated Dec. 23, 2020 (N&V Ref.: 4403-3977).
Correction of Inventorship and Declaration of Inventorship for NZ Application No. 765654, four pages, dated Jan. 26, 2021 (N&V Ref.: 4403-3977).
Letters Patent from the IPONZ, for NZ Application No. 762904, one page, issued Feb. 2, 2021 (N&V Ref.: 4403-3976).
Request for Correction of Error Accepted from the IPONZ, for NZ Application No. 765654, one page, dated Jan. 29, 2021 (N&V Ref.: 4403-3977).
Further Examination Report—Postponed Acceptance from the IPONZ, for NZ Application No. 765654, one page, dated Mar. 3, 2021 (N&V Ref.: 4403-3977).
Notice of Acceptance from the IPONZ, for NZ Application No. 765654, two pages, dated Mar. 22, 2021 (N&V Ref.: 4403-3977).
Request for Correction of Error Accepted from the IPONZ, for NZ Application No. 765032, one page, dated Jan. 29, 2021 (N&V Ref.: 4403-3978).
Notice of Acceptance from the IPONZ, for NZ Application No. 765702, two pages, dated Mar. 22, 2021 (N&V 4403-4039).
Further Examination Report—Postponed Acceptance from the IPONZ, for NZ Application No. 765509, dated Apr. 1, 2021 (N&V 4403-4040).
Further Examination Report—Postponed Acceptance from the IPONZ, for NZ Application No. 765032, one page, dated Apr. 1, 2021 (N&V Ref.: 4403-3978).
Response to Examination Report filed with IPONZ, for NZ Application No. 765654, two pages, dated Feb. 17, 2021 (N&V Ref.: 4403-3977).
Response to Further Examination Report filed with IPONZ, for NZ Application No. 765032, four pages, dated Mar. 22, 2021 (N&V Ref.: 4403-3978).
Response to Further Examination Report filed with IPONZ, for NZ Application No. 765509, dated Mar. 22, 2021 (N&V 4403-4040).

\* cited by examiner

FLOW GENERATOR MESSAGE SYSTEM

CROSS-REFERENCES TO RELATED APPLICATIONS

This application is a continuation of U.S. patent application Ser. No. 16/103,258, filed Aug. 14, 2018, now allowed; which is a continuation of U.S. patent application Ser. No. 14/665,192, filed Mar. 23, 2015, now U.S. Pat. No. 10,076,617, issued Sep. 18, 2018; which is a continuation of U.S. patent application Ser. No. 13/845,413, filed Mar. 18, 2013, now U.S. Pat. No. 9,010,328, issued Apr. 21, 2015; which is a divisional of U.S. patent application Ser. No. 12/067,234, filed Nov. 14, 2008, now U.S. Pat. No. 8,424,514, issued Apr. 23, 2013; which is the U.S. National Stage of International Application No. PCT/AU2006/001506, filed Oct. 13, 2006; which claims the benefit of Provisional Application No. 60/726,178, filed Oct. 14, 2005, the entire contents of which are incorporated herein by reference.

STATEMENT REGARDING FEDERALLY SPONSORED RESEARCH OR DEVELOPMENT (NOT APPLICABLE)

BACKGROUND OF THE INVENTION

The present invention relates generally to flow generators for ventilatory assistance and, more particularly, to a flow generator that includes a message system for communicating messages relating to flow generator operation, flow generator service, flow generator use, patient health, peripheral devices and services, patient treatments, general reminders, and the like. Messages may be delivered to an onboard display or externally to a service provider, the patient, a physician, or the like.

Non-Invasive Positive Pressure Ventilation (NIPPV) is a form of treatment for breathing disorders which can involve providing a relatively higher pressure of air or other breathable gas to the entrance of a patient's airways via a patient interface (e.g., a mask) during the inspiratory phase of respiration, and providing a relatively lower pressure or atmospheric pressure in the patient mask during the expiratory phase of respiration. In other NIPPV modes the pressure can be made to vary in a complex manner throughout the respiratory cycle. For example, the pressure at the mask during inspiration or expiration can be varied through the period of treatment.

Continuous Positive Airway Pressure (CPAP) treatment is commonly used to treat breathing disorders including Obstructive Sleep Apnea (OSA). CPAP treatment continuously provides pressurized air or other breathable gas to the entrance of a patient's airways via a patient interface (e.g., a mask) at a pressure elevated above atmospheric pressure, typically in the range 3-20 cm $H_2O$. CPAP treatment can act as a pneumatic splint of a patient's upper airway.

CPAP treatment can be in a number of forms, including the maintenance of a constant treatment pressure level, alternating between two different constant levels in synchronism with the inspiratory and expiratory phases of respiration ("bi-level CPAP"), and having an automatically adjustable and/or a computer controlled level in accordance with a patient's therapeutic needs.

Breathable gas supply apparatus used in CPAP and NIPPV treatments broadly comprise a flow generator constituted by a continuous source of air or other breathable gas generally in the form of a blower driven by an electric motor. A pressurized supply of air or other breathable gas can also be used. The gas supply is connected to a conduit or tube, which is in turn connected to a patient interface (mask or nasal prong) which incorporates, or has in close proximity, a vent to atmosphere for exhausting exhaled gases, such as carbon dioxide.

BRIEF SUMMARY OF THE INVENTION

Patients using flow generators necessarily integrate the devices into their sleeping routine. The devices are used on a daily basis and greatly enhance the quality of life for patients requiring them. It would thus be desirable if the flow generators themselves could communicate with the users to maximize system effectiveness and therapy and facilitate use of the device in the patients' daily lives.

In this context, it is important that the device function and be operated properly, and it is desirable to enable the device to introspectively determine operating concerns or malfunctions. The present invention provides a flow generator that generates messages to facilitate use of the device. The messages may relate to aspects of the flow generator itself or to integrating the system into a patient's daily routine. The messages can be delivered over any suitable medium in any suitable manner, such as for example by written, graphical or audible messages. A related flow generator with a patient reminder system is disclosed in U.S. patent application Ser. No. 10/533,940, the contents of which are hereby incorporated by reference.

In an exemplary embodiment of the invention, a flow generator for delivering breathable gas to a patient includes a processor coupled with operation sensors and a user interface. The processor is programmed to generate one of time-based messages, event-based messages, or both time- and event-based messages relating to at least one of flow generator operation, flow generator service, flow generator use, patient health, peripheral devices and services, patient treatment, and general reminders. The time-based messages are generated at predetermined time intervals based on either time of use or elapsed time, and the event-based messages are generated based on signals from the operation sensors. The user interface is configured to deliver the messages to at least one of a display, a flow generator service provider, the patient and a physician.

The processor is preferably programmed to receive a reminder request input, wherein the time-based messages include reminders generated at a time specified in the reminder request input. The user interface may include a wireless communication system that communicates with at least one of a preset telephone number, a cellular phone, a pager, and a call center.

In one embodiment, the user interface is a network interface that delivers the messages via a global network such as the internet. In this context, the event-based messages may comprise messages relating to flow generator parts requiring replacement or repair. Moreover, the system may automatically order at least one of the parts requiring replacement or service for the repair. The network interface is preferably also configured to receive message content via the global network. The message content may comprise information relating to new products and peripherals cooperatively usable with the flow generator.

The flow generator may additionally include a memory that stores software executed by the processor and data relating to flow generator use and operation. The processor executes the software to generate the messages. In one embodiment, the memory is a data card.

The flow generator may still additionally include peripheral devices providing enhanced functionality. The peripheral devices communicate with the processor, wherein the time-based and event-based messages relate to use and operation of the peripheral devices.

The time-based messages may be customizable, for example, providing a personal reminder for the patient, a wake-up alarm or the like. The wake-up alarm may be an audio message or may be effected via the delivery of breathable gas to the patient. The messages may include advertisements generated at predetermined time intervals and/or upon the occurrence of at least one event relating to flow generator use and operation. The messages may relate to helpful user tips and may be interactive with the patient.

The event-based messages may be structured as notice levels relating to flow generator operation, where the notice levels are changed based on a use condition duration detected by the sensors. In one embodiment, the use condition is a leak, wherein a first notice level provides an indication that the leak has been detected, a second notice level provides another indication that the leak has been detected along with user tips to correct the leak, and a third notice level provides a communication notifying a service provider or physician of the leak.

In another exemplary embodiment of the invention, a CPAP apparatus includes a flow generator that generates a supply of pressurized air to be provided at an outlet; a patient interface engageable with a patient's face to provide a seal; and an air delivery conduit coupled between the flow generator and the patient interface to deliver the supply of pressurized air from the flow generator to the patient interface. The flow generator preferably includes a processor coupled with operation sensors and a user or communication interface.

In yet another exemplary embodiment of the invention, an identifier is provided for use with a flow generator that generates a supply of pressurized air to be provided at an outlet to a patient for treatment. The flow generator includes a processor coupled with operation sensors and a user interface, wherein the processor is programmed to generate time-based and/or event-based messages relating to at least one of flow generator operation, flow generator service, flow generator use, patient health, peripheral devices and services, patient treatment, and general reminders, wherein the time-based messages are generated at predetermined time intervals based on either time of use or elapsed time, and wherein the event-based messages are generated based on signals from the operation sensors. The identifier includes an identifying element providing an identifying feature unique to a specific peripheral component attachable to the flow generator. The processor discerns the specific peripheral component via the identifying feature. In this context, the time-based and event-based messages are generated based on use and operation of the specific peripheral component.

In still another exemplary embodiment of the invention, a method is provided for operating a flow generator that generates a supply of pressurized air to be provided at an outlet to a patient for treatment, the flow generator including a processor coupled with operation sensors and a user interface. The method includes the steps of generating either time-based or event-based messages relating to at least one of flow generator operation, flow generator service, flow generator use, patient health, peripheral devices and services, patient treatment, and general reminders, the time-based messages being generated at predetermined time intervals based on either time of use or elapsed time, and the event-based messages being generated based on signals from the operation sensors; and delivering the messages via the user interface to at least one of a display, a flow generator service provider, the patient and a physician.

BRIEF DESCRIPTION OF THE DRAWINGS

These and other aspects and advantages of the present invention will be described in detail with reference to the accompanying drawings, in which.

DETAILED DESCRIPTION OF PREFERRED EMBODIMENTS

Flow Generator

Figure 1:
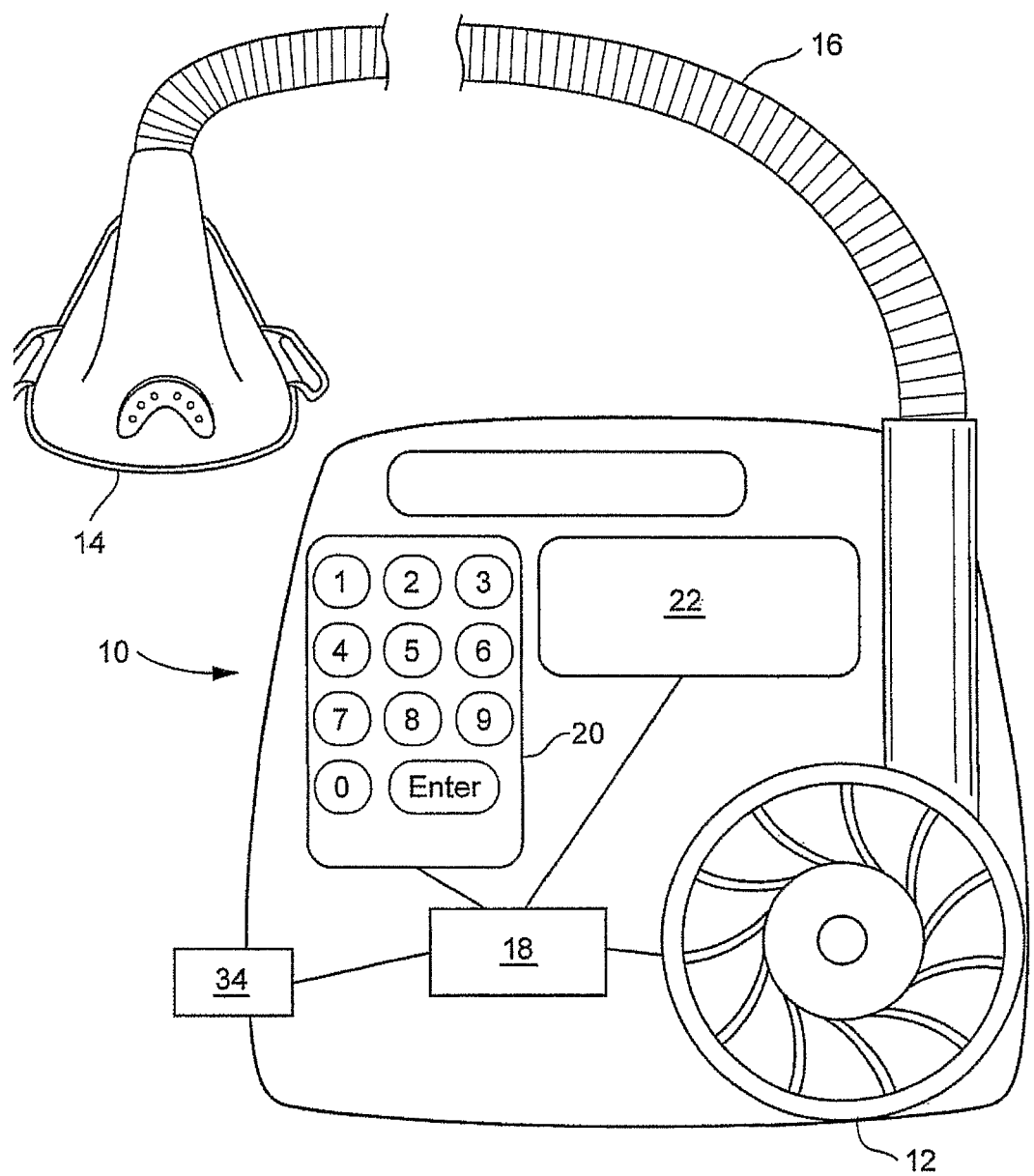
FIG. 1 is a perspective view of an exemplary flow generator.

The concepts of the present invention are suitable for any flow generator providing NIPPV and/or CPAP treatment, including but not limited to flow generators having motor controlled pressure regulation or valve pressure regulation. An exemplary flow generator structure will be described with reference to FIG. 1 for purposes of explanation.

A flow generator 10 includes a motor 12 that provides a supply of pressurized air for the administration of NIPPV and/or CPAP treatment. The pressurized air is delivered to a patient via a patient interface 14. An air delivery conduit 16 is coupled between the flow generator 10 and the patient interface 14. The patient interface 14 may have any suitable configuration as is known in the art, e.g., full-face mask, nasal mask, oro-nasal mask, mouth mask, nasal prongs, etc. Furthermore, the patient interface 14 also encompasses both vented and non-vented masks and dual limb mask systems. A processor 18 controls the operations of the flow generator. The flow generator is provided with a user interface unit or "communication system" 20 (which is generically intended to encompass both input and output systems of any suitable structure) to allow information input and a display unit 22 to display output information.

Communication System

Figure 2:
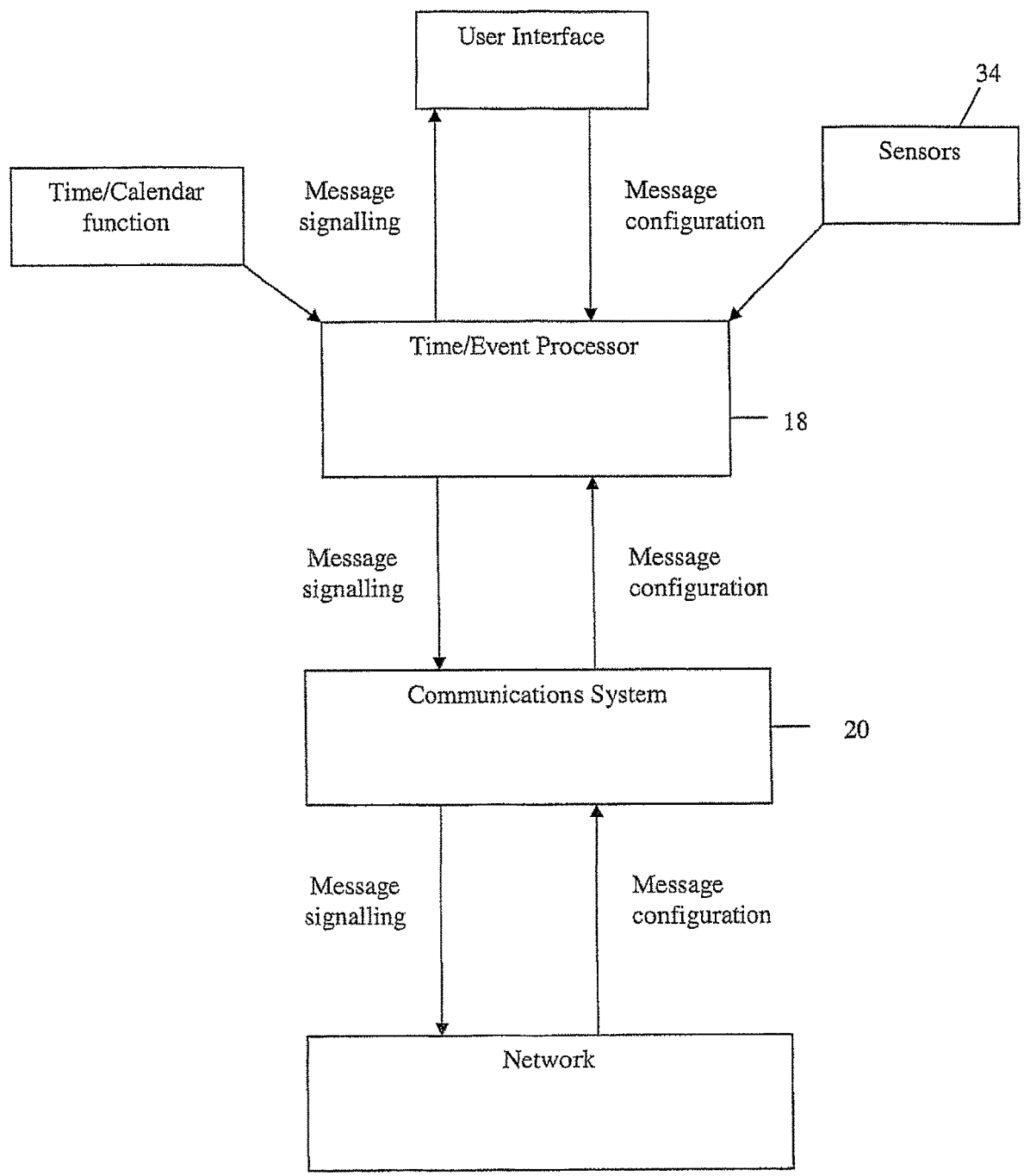
FIG. 2 is a schematic block diagram of the flow generator operating system and message/alarm functionality.

With reference to FIG. 2, the processor is coupled with the operation sensors (shown schematically at 34) and communication system 20. The processor is programmed to generate time-based or event-based messages relating to one or more of flow generator operation, flow generator service, flow generator use, patient health, peripheral devices and services, patient treatment, and general reminders or the like. The user interface or communications system 20 includes structure that effects delivery of the messages. Delivery of messages may be via the display unit 22 or via an external communication device such as a modem or wireless technology such as cellular telephony or via the internet through a network interface. With a remote communication system, the flow generator can also deliver messages to a physician, a flow generator service provider, the patient, or the like.

Time-Based Messages

The messages generated by the processor 18 may be time-based or event-based or both. Time-based messages are generated at predetermined time intervals based on either time of use or elapsed time. Examples of time-based messages include general reminders, where the processor is programmed to receive a reminder request input, and the messages comprise reminders generated at a time specified in the reminder request input. Examples of other time-based messages may include a notice that one or more parts should be replaced (after a certain period of use), a reminder concerning timing for a patient to schedule an appointment with their physician, a wake-up alarm, which may be an audible alarm or may be effected via the delivery of breathable gas to the patient such as via pulses of air or by pressure variations, and the like. The time-based messages may be customizable by the patient for use as a personal reminder. For example, the flow generator may be programmed to remind the patient to take their pills. Advertisements may also be generated at predetermined time intervals, possibly in relation to a time interval when a part such as the mask or filter should be replaced.

The time-based messages may also include helpful user tips to assist the user in maximizing flow generator functionality. A calendar and clock function enables use of the system to generate wake-up alarms as well as provide time-based messages based on either time of use or elapsed time. An example of a flow generator including a built in alarm clock is disclosed in U.S. Patent Application Ser. No. 60/703,432, filed Jul. 29, 2005, the contents of which are hereby incorporated by reference. Helpful tips and other use information can thus be provided to the patient based on the time of year. For example, the processor may be programmed such that it knows winter months are approaching (i.e., from the calendar) and can remind the patient to utilize their humidifier. In addition, the calendar and clock function can monitor user sleep cycle and awaken the user at non-REM sleep.

Event-Based Messages

Event-based messages are generated based on signals from the operation sensors 34 and are correlated to particular events or triggers detected by the processor 18 via the sensors 34. For example, the event-based messages may relate to flow generator parts requiring replacement or repair. The processor 18 can determine via the sensors 34 whether a particular part needs replacement or repair. For example, if a leak is detected in the mask, it may be that the mask needs to be replaced. The system may effect automatic ordering of one or more of the parts requiring replacement or generate a request for service or repair, which may be part of a user subscription. In concert with such a determination, the processor 18 may generate helpful tips to assist the user in properly positioning/wearing the mask. The processor 18 may generate advertisements as event-based messages, for example when parts need replacement or as new parts/products become available. In this context, the communication system 20 may be capable of receiving data as message content for example via the global network through the network interface. In this manner, the message content may include information relating to new products and peripherals cooperatively usable with the flow generator.

Peripheral Devices

The flow generator may additionally include peripheral devices providing enhanced functionality. In this context, the peripheral devices may be detected via an identifier including an identifying element providing an identifying feature unique to a specific peripheral component attachable to the flow generator. The processor 18 discerns the specific peripheral component (e.g., patient interface) via the identifying feature. This concept is described in detail in commonly-owned U.S. patent application Ser. No. 60/656,880, the contents of which are hereby incorporated by reference. In this manner, the messages generated by the processor 18 may relate to use and operation of the peripheral devices.

Notice Levels

In one embodiment, the event-based messages include notice levels relating to flow generator operation. The notice levels are changed based on a use condition duration detected by the sensors 34. For example, a use condition may be a leak at the mask. In this context, a first notice level may include an indication that the leak has been detected, a second notice level may include another indication that the leak has been detected along with user tips to correct the leak, and a third notice level may include a communication notifying a service provider or physician of the leak.

AHI Threshold

A patient's specific AHI (apnea-hyponea index) threshold may be entered into the device and monitored as an indicator of the effectiveness of the therapy. AHI is a measure of the number of apnea or hypopnea events that occur per hour of sleep, which is used to assess the severity of sleep disordered breathing (SDB). Commonly, an AHI of 5 or greater is considered to indicate mild OSA. Thus the AHI will vary amongst different patients, and consequently an AHI threshold will also vary between patients. The AHI threshold may be determined and entered by a clinician for an individual patient. The AHI or AHI threshold is an example of an event that may be monitored and reported on using the messaging system of the present invention. A change in the AHI index may be considered an indicator of how effective the therapy has been. For example a decrease in the AHI would indicate that the therapy was having a positive effect.

Monitoring System

A remote monitoring system is described in the U.S. patent application Ser. No. 10/934,540, the contents of which are hereby incorporated by reference. This system is not present in the flow generator but is a patient server comprising a database of rules governing payment of home care devices and the details for patients and devices. The system monitors when a patient is eligible to receive payment for further home-care devices and may generate a reminder letter to send to the patient; thus reminding and encouraging patients to update their devices. The system may also be used to monitor drug prescription requirements. This type of reminder may also be included in the present application such that the reimbursement or payment details for a patient are entered into the device or may be selected from a list, and then in a similar manner the device will remind the patient when they are eligible to purchase further equipment.,

CONCLUSION

The flow generator of the invention includes a message generating capability and communication structure that facilitate and enhance its use. The ability to communicate information to the user will reduce users' needs to contact the physician or product supplier with questions. The system can record events thereby reducing the burden and therefore labor and costs for processing insurance coverage. A calendar and clock function enables use of the system to generate wake-up alarms as well as provide time-based messages based on either time of use or elapsed time. Sensors enable the system to generate event-based messages. Of course, the examples described herein are exemplary, and those of ordinary skill in the art will appreciate that many variations of messages may be generated by the flow generator of the invention, and the invention is not necessarily meant to be limited to the described examples.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

The invention claimed is:

1. A flow generator for use in a continuous positive airway pressure (CPAP) system or a non-invasive positive pressure ventilation (NIPPV) system, the flow generator comprising:
   a motor configured to generate a supply of breathable gas for delivery to a patient;
   at least one operation sensor;
   at least one processor configured to:
      receive signals from the at least one operation sensor;
      during operation of the flow generator while the supply of breathable gas is delivered to the patient, detect an indication of a leak based on the signals from the at least one operation sensor;
      based on the indication of the leak, generate a first message;
      cause the first message to be communicated;
      during operation of the flow generator while the supply of breathable gas is delivered to the patient, detect a further indication of the leak based on the signals from the at least one operation sensor;
      based on the further indication of the leak, generate a second message; and
      cause the second message to be communicated, wherein the second message is different from the first message.

2. The flow generator of claim 1, wherein the first message and/or the second message includes an indication that the leak has been detected.

3. The flow generator of claim 2, wherein the first message and/or the second message includes an indication that the leak has been detected.

4. The flow generator of claim 3, wherein the first message and/or the second message includes tips to correct the leak.

5. The flow generator of claim 4, wherein the tips include tips related to positioning and/or wearing a patient interface.

6. The flow generator of claim 1, wherein the at least one processor is further configured to:
   determine a leak duration based on the signals from the at least one operation sensor.

7. The flow generator of claim 6, wherein the second message is generated further based on the determined leak duration.

8. The flow generator of claim 1, wherein the first message is output to a display device that is coupled to the flow generator.

9. The flow generator of claim 8, further comprising the display device.

10. The flow generator of claim 1, wherein the first message is communicated to a different destination than the second message.

11. The flow generator of claim 1, wherein the first message is communicated to a display device that is provided in the flow generator and the second message is communicated over an electronic data network to a remote computing device.

12. The flow generator of claim 1, wherein the at least one processor is further configured to
   during operation of the flow generator while the supply of breathable gas is delivered to the patient, detect a third indication of the leak based on the signals from the at least one operation sensor;
   based on the third indication of the leak, generate a third message; and
   cause the second message to be communicated, wherein the third message is different from both the first and second messages.

13. The flow generator of claim 12, wherein
   the first message includes a notice of the leak, the second messages includes tips for correcting the leak, and the third message is communicated to an external destination that is associated with a service provides and/or a physician.

14. The flow generator of claim 1, wherein the at least one processor is further configured to:
   determine an identifying feature that is associated at least one component of the CPAP system or NIPPV system; and
   control at least one operating parameter of the flow generator based on the determined identifying feature.

15. The flow generator of claim 1, wherein the flow generator is configured to deliver the supply of breathable gas to the patient via an air conduit and a patient interface, wherein the air conduit and the patient interface are fluidly coupled to the flow generator.

16. The flow generator of claim 15, wherein the leak is a leak in the patient interface.

17. The flow generator of claim 15, wherein the first message and/or the second message includes tips to correct the leak, wherein the tips include tips related to positioning and/or wearing a patient interface.

18. A method performed on a flow generator that includes at least one processor, the method comprising:
   receiving signals from at least one operation sensor;
   during operation of the flow generator and while a supply of breathable gas is delivered to a patient, determining an indication of a leak based on the signals from the at least one operation sensor;
   based on the indication of the leak, generating a first message;
   causing the first message to be communicated;
   during operation of the flow generator while the supply of breathable gas is delivered to the patient, determining a further indication of the leak based on the signals from the at least one operation sensor;
   based on the further indication of the leak, generating a second message; and
   causing the second message to be communicated, wherein the second message is different from the first message.

19. The method of claim 18, wherein the first message is communicated to a different destination than the second message.

20. The method of claim 18, further comprising:
   determining a leak duration based on the signals from the at least one operation sensor,
   wherein the second message is generated further based on the determined leak duration.

* * * * *